United States Patent
Ishikawa et al.

(10) Patent No.: US 6,932,975 B2
(45) Date of Patent: Aug. 23, 2005

(54) COSMETIC COMPOSITION COMPRISING A PHOSPHORIC TRIESTER AND A SKIN ACTIVATING COMPONENT

(75) Inventors: Shinji Ishikawa, Tokyo (JP); Masanori Tanahashi, Tokyo (JP); Tomohiko Sano, Tokyo (JP); Ichiro Sugai, Tokyo (JP)

(73) Assignee: Kao Corporation, Tokyo (JP)

( * ) Notice: Subject to any disclaimer, the term of this patent is extended or adjusted under 35 U.S.C. 154(b) by 33 days.

(21) Appl. No.: 09/341,706

(22) PCT Filed: Jan. 22, 1998

(86) PCT No.: PCT/JP98/00239

§ 371 (c)(1),
(2), (4) Date: Jul. 28, 1999

(87) PCT Pub. No.: WO98/32419

PCT Pub. Date: Jul. 30, 1998

(65) Prior Publication Data

US 2002/0187166 A1 Dec. 12, 2002

(30) Foreign Application Priority Data

| Jan. 29, 1997 | (JP) | 9-015136 |
| Jan. 29, 1997 | (JP) | 9-015137 |
| Sep. 4, 1997 | (JP) | 9-239486 |

(51) Int. Cl.[7] ............ A61K 6/00; A61K 7/06; A61K 7/42; A61K 7/44; A61K 7/021

(52) U.S. Cl. ............ 424/401; 424/59; 424/60; 424/61; 424/62; 424/63; 424/64; 424/69; 424/70.1; 424/70.3; 424/70.6; 424/70.7; 424/70.8; 424/70.9

(58) Field of Search ............ 424/60–64, 70.1, 424/401, 59, 70.3, 70.6, 70.7–70.9, 70.11, 74, 69; 514/438, 141, 144

(56) References Cited

U.S. PATENT DOCUMENTS

| 4,140,647 A | * | 2/1979 | Mizutani et al. ............ 252/89 R |
| 5,053,220 A | * | 10/1991 | Arraudeau et al. |
| 5,603,939 A | * | 2/1997 | Ser |
| 5,750,487 A | * | 5/1998 | Oldenhove et al. ......... 510/365 |
| 5,904,735 A | * | 5/1999 | Gutierrez et al. ............ 8/137 |
| 6,299,887 B1 | * | 10/2001 | Yano et al. ................. 424/401 |

FOREIGN PATENT DOCUMENTS

| JP | 8183723 A | 7/1996 |
| JP | 8231565 A | 9/1996 |
| JP | 8310935 A | 11/1996 |
| JP | 9067224 A | 3/1997 |
| JP | 9165313 A | 6/1997 |

OTHER PUBLICATIONS

Translation of JP 58–131912, published Aug. 1983 by Hiroshi Takahashi.*

G. G. Hawly, The Condensed Chemical Dictionary, 10th Ed., Van Nostrand Reinhold Co., New York (1981), p. 433.*

* cited by examiner

Primary Examiner—Shengjun Wang
(74) Attorney, Agent, or Firm—Oblon, Spivak, McClelland, Maier & Neustadt, P.C.

(57) ABSTRACT

A cosmetic comprising (A) a phosphoric triester represented by the general formula (1):

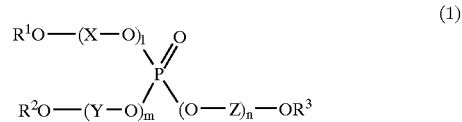

wherein $R^1$ and $R^2$ are independently an alkyl group having 1 to 8 carbon atoms, $R^3$ is an alkyl group having 1 to 4 carbon atoms, X, Y and Z are independently an alkylene group having 2 or 3 carbon atoms, l and m are independently a number of 1 to 10, and n is a number of 0 to 10, and (B) a skin activating component.

4 Claims, No Drawings

COSMETIC COMPOSITION COMPRISING A PHOSPHORIC TRIESTER AND A SKIN ACTIVATING COMPONENT

This application is a 371 of PCT/JP98/00239, filed Jan. 22, 1998, which claim priority of JP09-015136, filed Jan. 29, 1997, JP09-015137, filed Jan. 29, 1997, and JP09-239486, filed Sep. 4, 1997.

TECHNICAL FIELD

The present invention relates to a cosmetic which is excellent in preventing and remedying effects on a variety of cutaneous troubles and gives users a pleasant feeling upon use.

BACKGROUND ART

In recent years, it has been a matter of significant concern to maintain a healthy and beautiful skin irrespective of age or sex. However, the skin is delicately affected by aging, and besides temperature, humidity, ultraviolet rays, cosmetic products, diseases, stress, eating habits, etc. Therefore, various troubles such as the decrement of various functions (functions of preventing the loss of water and the like from the vital body to control the homeostatic maintenance of the body heat, protecting the body from physical and chemical stimulation and various bacteria and keeping the resilience of the skin to determine its surface form, and the like) of the skin and aging of the skin occur.

Further, the cutaneous troubles occur due to, in addition to the functional aberration of skin tissue caused by intracorporeal and extracorporeal factors, which act on the vital body, such as changes of the external environments (seasonal changes, ultraviolet rays, etc.) and variations in physiological functions attendant on aging or diseases as described above, pachymenia, parakeratosis and the like induced thereby.

On the other hand, wrinkles, which are one of dermal troubles, occur due to dermal aging caused by aging, drying, ultraviolet rays and/or the like. More specifically, the skin is aged by morphological changes of the epidermal surface caused by physical and chemical stimulation from the external world, such as drying and ultraviolet rays, and tissue degeneration in the dermis by aging, diseases, stress and the like, particularly, deterioration of the dermis, in which collagen fibers are lost to a great extent, reduction of subcutaneous adipose tissue and the like, which the aging mainly forms the cause of wrinkles, slackness and loss of resilience.

Spots and freckles on the skin are generally considered to be caused by the abnormal pigmentation of melanin pigment within the skin; the melanin pigment is synthesized in melanocytes activated by the cause such as stimulation by exposure to ultraviolet rays from sunlight, hormone aberration or genetic factors.

As principal attempts for preventing and remedying such cutaneous troubles, there has been carried out a method in which a synthetic or natural moisturizer is applied to the skin, thereby preventing the drying of the skin to enhance the moistening ability of the skin; a method in which a blood circulation-facilitating agent is applied to the skin, thereby facilitating the circulation of blood; the development of agents for preventing wrinkles (Japanese Patent Application Laid-Open Nos. 185005/1987, 502546/1987, 72157/1990 and 288822/1990, etc.); the application of a whitening agent such as a melanin inhibitor; or the like.

However, all these means have not attained a sufficient effect on the cutaneous troubles.

It is accordingly an object of the present invention to provide a cosmetic which is excellent in preventing and remedying effects on the above-described cutaneous troubles and gives users a pleasant feeling upon use.

DISCLOSURE OF THE INVENTION

In view of the foregoing circumstances, the present inventors have carried out an extensive investigation. As a result, it has been found that when a specific phosphoric triester and a skin activating component are used in combination, the phosphoric triester facilitates the penetration of the skin activating component to synergistically enhance the effects of the skin activating component, i.e., the moisturizing effect, the effects of preventing and remedying skin roughness, the effects of preventing the firm and resilient skin from declining and remedying the declined skin, the effects of preventing a complexion from dulling and remedying a dull looking face, the effects of preventing and remedying the conspicuousness of pores of the skin and pimples caused by excess sebum, microorganisms or keratonosis, the effects of preventing development of wrinkles and remedying the wrinkled skin, and the effects of preventing and remedying spots and freckles, and so a cosmetic which can effectively remedy the above-described cutaneous troubles and gives users a pleasant feeling upon use is provided, thus leading to completion of the present invention.

According to the present invention, there is thus provided a cosmetic comprising the following components (A) and (B):

(A) A Phosphoric Triester Represented by the General Formula (1):

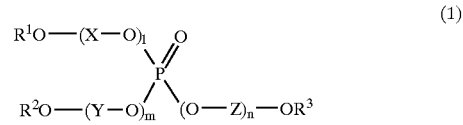

wherein $R^1$ and $R^2$ are the same or different from each other and independently a linear or branched alkyl group having 1 to 8 carbon atoms; $R^3$ is a linear or branched alkyl group having 1 to 4 carbon atoms; X, Y and Z are the same or different from one another and independently a linear or branched alkylene group having 2 or 3 carbon atoms; l and m are the same or different from each other and independently a number of 1 to 10, and n is a number of 0 to 10; and (B) A Skin Activating Component.

According to the present invention, there is also provided a method for improving the efficacy of a skin activating component, which comprises incorporating a phosphoric triester of the general formula (1) into a cosmetic composition comprising the skin activating component.

According to the present invention, there is further provided use of a phosphoric triester of the general formula (1) as an efficacy improving agent for a skin activating component.

BEST MODE FOR CARRYING OUT THE INVENTION

The phosphoric triester of the component (A) used in the present invention is a compound represented by the general formula (1).

Examples of the linear or branched alkyl groups having 1 to 8 carbon atoms represented by $R^1$ and $R^2$ in the general formula (1) include methyl, ethyl, n-propyl, isopropyl, n-butyl, isobutyl, n-pentyl, n-hexyl, heptyl, octyl and 2-ethylhexyl groups. Of these, those having 2 to 6 carbon atoms are preferred, with those having 2 to 4 carbon atoms being particularly preferred from the viewpoints of low irritativeness and a good feeling upon use. $R^1$ and $R^2$ may be the same or different from each other from the viewpoint of the performance of the phosphoric triester, but are preferably the same from the viewpoint of easy synthesis.

Examples of the linear or branched alkyl group having 1 to 4 carbon atoms represented by $R^3$ in the general formula (1) include methyl, ethyl, n-propyl, isopropyl, n-butyl and isobutyl groups. Of these, ethyl and n-butyl groups are preferred, with ethyl group being particularly preferred.

Examples of the linear or branched alkylene groups having 2 or 3 carbon atoms represented by X, Y and Z in the general formula (1) include ethylene, trimethylene and propylene groups. Of these, the ethylene group is preferred. The numbers of 1 to 10 represented by l, m and n indicate average numbers of moles of XO, YO and ZO added, respectively. The portions of $(XO)_l$, $(YO)_m$ and $(ZO)_n$ may be each single or have a distribution. l and m are each preferably a number of 1 to 5, more preferably 1 to 4, particularly 2 or 3. n is preferably 0 or a number of 1 to 5, more preferably 0 or 1 to 4.

Preferable examples of the phosphoric triester of the component (A) include those in which in the general formula (1), $R^1$, $R^2$ and $R^3$ are independently an alkyl group having 2 to 4 carbon atoms, X, Y and Z are all ethylene groups, and l, m and n are independently a number of 1 to 4. In the general formula (1), those are also preferred wherein $R^1$ and $R^2$ are independently an alkyl group having 2 to 6 carbon atoms, X and Y are both ethylene groups, n is a number of 0, and l and m are independently a number of 1 to 5.

The phosphoric triester (1) can be synthesized by reacting 3 alcohols represented by $R^1O—(X—O)_l—H$, $R^2O—(Y—O)_m—H$ and $R^3O-(Z-O)_n—H$ (when two or all of the three groups of the intended product are the same, two or one alcohol thereof) together or successively with a phosphorus oxyhalide, for example, phosphorus oxychloride either directly or in the presence of a base in accordance with a publicly known method.

No solvent may be used specially. If used, examples thereof include ether solvents, aliphatic hydrocarbons, alicyclic hydrocarbons and aromatic hydrocarbons.

Examples of the base usable in this reaction include organic tertiary amines such as triethylamine, tributylamine and pyridine, and alkali metal hydroxides such as sodium hydroxide and potassium hydroxide.

Specific examples of the phosphoric triester (1) of the component (A) include the following compounds:

(a) tris(butoxyethyl) phosphate, (b) tris (butoxyethoxyethyl) phosphate, (c) tris (butoxyethoxyethoxyethyl) phosphate, (d) tris (ethoxyethoxyethyl) phosphate, (e) tris (ethoxyethoxyethoxyethyl) phosphate, (f) tris (methoxyethoxyethyl) phosphate, (g) tris (methoxyethoxyethoxyethyl) phosphate,

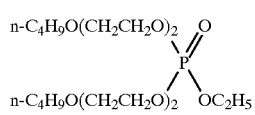

(h)

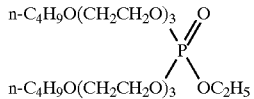

(i)

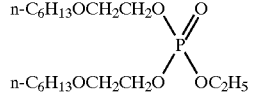

(j)

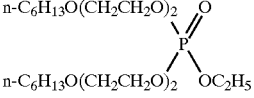

(k)

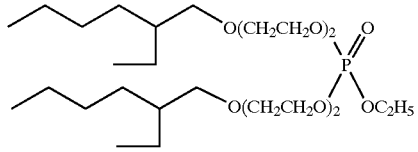

(l)

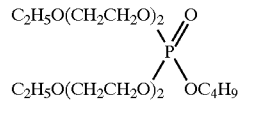

(m)

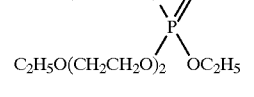

(n)

The phosphoric triesters may be used as the component (A) either singly or in any combination thereof and are preferably incorporated in a proportion of 1 to 50% by weight, more preferably 2 to 25% by weight, particularly 5 to 20% by weight based on the total weight of the cosmetic composition.

The skin activating component of the component (B) used in the present invention is a substance having some effect on the skin, for example, moisturizing effect, skin-softening effect, whitening effect, anti-inflammatory effect, anti-oxidant effect, blood circulation-facilitating effect, sebum secretion-inhibiting effect, etc. No particular limitation is imposed on such activating components so far as they are various kinds of activating ingredients commonly used in the classical cosmetic products, quasi-drugs, drugs and the like. Examples thereof include ceramides, pseudoceramides, hydrophilic moisturizers, amino acids, plant extracts, whitening agents, anti-inflammatory agents, singlet oxygen scavengers, antioxidants, water-soluble polymers, alcohols, sterols, blood circulation-facilitating agents, sebum secretion inhibitors, anti-microbial agents, keratolytic agents, etc.

Of these, the ceramides are publicly known compounds represented by the following general formula (2):

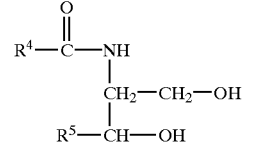

(2)

wherein $R^4$ and $R^5$ are the same or different from each other and independently a linear or branched and saturated or unsaturated hydrocarbon group having 8 to 26 carbon atoms.

$R^4$ is preferably a linear alkyl group having 15 to 23 carbon atoms, particularly a pentadecyl, heptadecyl or tricosyl group, while $R^5$ is preferably a linear and saturated or unsaturated alkyl or alkenyl group having 15 to 23 carbon atoms, particularly a pentadecyl, heptadecyl or heptadecenyl group.

Examples of the pseudoceramides include those represented by the following general formulae (3) to (7):

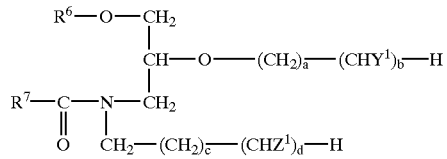

(3)

wherein $R^6$ is a linear or branched and saturated or unsaturated hydrocarbon group having 10 to 26 carbon atoms, $R^7$ is a linear or branched and saturated or unsaturated hydrocarbon group having 9 to 25 carbon atoms, and $Y^1$ and $Z^1$ are independently a hydrogen atom or hydroxyl group, a is a number of 0 or 1, c is a number of 0 to 4, and b and c are independently a number of 0 to 3;

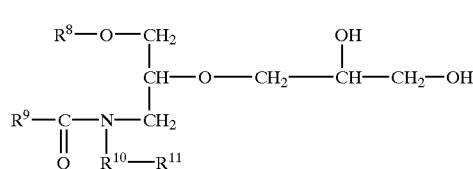

(4)

wherein $R^8$ and $R^9$ are the same or different from each other and independently a linear or branched and saturated or unsaturated hydrocarbon group having 1 to 40 carbon atoms, which may be hydroxylated, $R^{10}$ is a linear or branched alkylene group having 1 to 6 carbon atoms or a single bond, and $R^{11}$ is a hydrogen atom, a linear or branched alkoxy group having 1 to 12 carbon atoms or a 2,3-dihydroxypropyloxy group, with the proviso that when $R^{10}$ is a single bond, $R^{11}$ is a hydrogen atom;

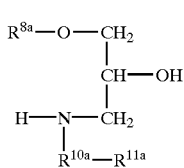

(5)

wherein $R^{8a}$ is a hydrocarbon group having 4 to 40 carbon atoms, which may be hydroxylated, $R^{10a}$ is a linear or branched alkylene group having 3 to 6 carbon atoms, and $R^{11a}$ is a linear or branched alkoxy group having 1 to 12 carbon atoms;

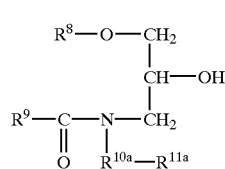

(6)

wherein $R^8$, $R^9$, $R^{9a}$ and $R^{10a}$ have the same meanings as defined above; and

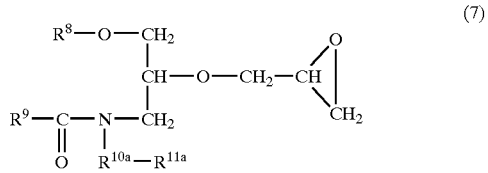

(7)

wherein $R^8$, $R^9$ and $R^{10}$ have the same meanings as defined above, and $R^{11b}$ is a hydrogen atom, a linear or branched alkoxy group having 1 to 12 carbon atoms or a 2,3-epoxypropyloxy group, with the proviso that when $R^{10}$ is a single bond, $R^{11b}$ is a hydrogen atom.

These pseudoceramides can be prepared in accordance with the publicly known methods [for example, Polish Journal of Chemistry, 52, 1059 (1978); ibid., 52, 1283 (1978); Japanese Patent Application Laid-Open Nos. 117421/1979, 144308/1979, 147937/1979, 228048/1987, 216852/1988 and 319263/1996].

$R^6$ is preferably a linear saturated alkyl group having 11 to 18 carbon atoms, particularly a tetradecyl, hexadecyl or octadecyl group, while $R^7$ is preferably a linear saturated alkyl group having 9 to 18 carbon atoms, particularly a nonyl, pentadecyl or heptadecyl group.

$R^8$ and $R^{8a}$ are each preferably a linear or branched alkyl or alkenyl group having 8 to 26 carbon atoms, while $R^9$ is preferably a linear or branched alkyl or alkenyl group having 9 to 25 carbon atoms.

$R^{10}$ and $R^{10a}$ are each preferably a linear alkylene group having 1 to 6 carbon atoms. Of these groups, methylene, ethylene and trimethylene groups are particularly preferred.

$R^{11}$, $R^{11a}$ and $R^{11b}$ are each preferably a hydrogen atom, an alkoxy group having 1 to 8 carbon atoms or a 2,3-dihydroxypropyloxy group.

These ceramides and pseudoceramides may be used either singly or in any combination thereof and are incorporated in a proportion of 0.01 to 50% by weight based on the total weight of the composition. It is more preferable to incorporate them in a proportion of particularly 0.01 to 20% by weight, more preferably 0.1 to 10% by weight from the viewpoints of a feeling upon use, the moisturizing effect, the effects of preventing and remedying skin roughness, the effects of preventing development of wrinkles and remedying the wrinkled skin, and stability.

Of the skin activating ingredients as the component (B), examples of the anti-microbial agents include sulfur, triclosan, trichlorocarbanilide, chlorhexidine hydrochloride, benzalkonium chloride, benzethonium chloride, cetylpyridinium chloride, benzalkonium alkylphosphates, isopropylmethylphenol, benzoic acid, photosensitive element No. 201 and resorcin. Of these, isopropylmethylphenol is particularly preferred. When these anti-microbial agents are incorporated, it is preferable to incorporate them in a proportion of 0.0001 to 5% by weight, particularly 0.001 to 2% by weight, more preferably 0.01 to 1% by weight based on the total weight of the composition.

Of the skin activating ingredients as the component (B), examples of the keratolytic agents include salicylic acid, N-acetylcysteine, lactic acid, citric acid, succinic acid, malic acid, alkylamine oxides and benzoyl peroxide. Of these, salicylic acid and citric acid are particularly preferred. When these keratolytic agents are incorporated, it is preferable to incorporate them in a proportion of 0.01 to 10% by weight, particularly 0.1 to 1% by weight based on the total weight of the composition.

Of the skin activating ingredients as the component (B), as the amino acids or salts thereof are preferred arginine, lysine, hydroxylysine and histidine, with arginine being particularly preferred.

These amino acids or salts thereof may be used either singly or in any combination thereof and are preferably incorporated in a proportion of 0.0001 to 15% by weight based on the total weight of the composition. It is more preferable to incorporate them in a proportion of particularly 0.001 to 10% by weight, more preferably 0.01 to 8% by weight from the viewpoints of the moisturizing effect, the effects of preventing development of wrinkles and remedying the wrinkled skin, the effects of preventing and remedying skin roughness, a feeling upon use, and stability.

Of the skin activating ingredients as the component (B), examples of the plant extracts include those obtained from plants such as *Angelica keiskei*, adzuki bean, catechu, avocado, hydrangea, *Gynostemma pentaphyllum*, althea, altheca, arnica, almond, aloe, apricot, nettle, iris, fennel, turmeric, rose fruit, pothos vine, Amur cork tree, goldthread, barley, gumbo, Saint-John's-wort, dead nettle, petty whiteroot, watercress, persimmon, puerariae root, *Valeriana fauriei*, birch, cattail, chamomile, *chamomilla*, oats, licorice, raspberry, kiwi, quinine tree, cucumber, apricot, coconut, Cape jasmine, *Sasa albo-marginata*, walnut, cinnamon, mulberry, GUNJO, gentian, cranesbill, sweet grass (*Magnoliae cortex*), ginseng, burdock, sesame, wheat, common comfrey, rice, *Camellia sasanqua*, saffron, Nippon hawthorn, Japanese pepper tree, mushroom, *Rehmannia glutinosa*, prop root, beefsteak plant, Japanese linden, Japanese spiraea, *Paeoniae radix*, ginger, ginger root, calamus, white birch, Japanese honeysuckle, field horsetail, *Stevia rebaudiana Bertoni*, western ivy, western hawthorn, elder, needle juniper, milfoil, mint, sage, common mallow, *Cnidii rhizoma*, Japanese green gentian, mulberry bark, soybean, *Zizyphi fructus*, thyme, tea, clove, dried orange peal, evening primrose, camellia, *Centella asiatica*, English walnut, *Angelica acutiloba*, pot marigold, ginseng, spruce, corn, *Houttuynia cordata*, tomato, carrot, garlic, wild rose, malt, ophopogon tuber, parsley, rye, adlay, Japanese mint, papaya, hamamelis, rose, white cedar, sunflower, loquat, coltsfoot, grapes, placenta, hazelnut, dishcloth gourd, safflower, *Tilia europaea* L, peony, hop, macadamia nut, pine, pinecorn, *marronnier*, melissa, melilot, peach, malt, Rodger's bronze leaf, palm, eucalyptus, creeping saxifrage, lily, *Coicis semen*, mugwort, rye, peanut, lavender, apple, litchi, lettuce, lemon, Chinese milk vetch, rosemary, scopolia, camomile, artemisia capillaris, agrimony, Japanese catalpa, *Thujopsis dolabrata*, HORUTOSO, *Isodon japonicus* Hara, orange pease, SENKISHI, chickweed, duckweed, mugwort, ginkgo, Chinese bellflower, chrysanthemum, *Sasa albo-marginata*, soapberry and weeping golden bell.

These plant extracts may be used either singly or in any combination thereof and are preferably incorporated in a proportion of 0.00001 to 20% by weight in terms of dry solids, based on the total weight of the composition. It is more preferable to incorporate them in a proportion of particularly 0.0001 to 10% by weight, more preferably 0.0001 to 5% by weight, since a cosmetic composition which has a moisturizing effect, the effects of preventing development of wrinkles and remedying the wrinkled skin, the effects of preventing and remedying skin roughness, the effects of preventing the firm and resilient skin from declining and remedying the declined skin, the effects of preventing a complexion from dulling and remedying a dull looking face, and the effects of preventing and remedying spots and freckles, gives users a more pleasant feeling upon use, and has far excellent stability can be provided.

When the extracts from one or more plants selected from among chamomile, tea, puerariae root, clove, licorice, loquat, spruce, ginseng, *Paeoniae radix*, Nippon hawthorn, ophopogon tuber, ginger root, pinecorn, mulberry bark, sweet grass, artemisia capillaris, catechu, pothos vine, aloe, althea, Japanese spiraea, watercress, quinine tree, common comfrey, rosemary and scopolia of these plant extracts are used, the whitening effect is synergistically enhanced, and so spots and freckles can be effectively prevented and remedied, and moreover the moisturizing effect and the effects of preventing and remedying skin roughness may also be markedly enhanced.

When the extracts from field horsetail, gentian, hamamelis, peony, agrimony, Japanese catalpa, *Thujopsis dolabrata*, ORUTOSO, *Isodon japonicus* Hara and orange pease of these plant extracts are used, the effect of preventing dermal aging is synergistically enhanced, and so development of wrinkles can be effectively prevented and the wrinkled skin can be effectively remedied, and moreover the moisturizing effect and the effects of preventing and remedying skin roughness may also be markedly enhanced.

No particular limitation is imposed on the whitening agents as the component (B) so far as they are those commonly used in the classical cosmetics, and examples thereof include L-ascorbic acid and derivatives thereof, hydroquinone derivatives such as arbutin, kojic acid and derivatives thereof, and placenta extracts.

These whitening agents may be used either singly or in any combination thereof and are preferably incorporated in a proportion of 0.01 to 30% by weight based on the total weight of the composition. It is more preferable to incorporate them in a proportion of particularly 0.01 to 10% by weight, more preferably 0.01 to 5% by weight, since a cosmetic composition which has a sufficient whitening effect, gives users a more pleasant feeling upon use, and has excellent stability can be provided.

Of the skin activating ingredients as the component (B), examples of the anti-inflammatory agents include glycyrrhizic acid and salts thereof, glycyrrhetinic acid and salts thereof, isopropylaminocapronic acid and salts thereof, allantoin, lysozyme hydrochloride, guaiazulene, methyl salicylate and γ-oryzanol. Of these, glycyrrhetinic acid, stearyl glycyrrhetinate and ε-aminocapronic acid are preferred.

These anti-inflammatory agents may be used either singly or in any combination thereof and are preferably incorporated in a proportion of 0.001 to 5% by weight based on the total weight of the composition. It is more preferable to incorporate them in a proportion of particularly 0.01 to 2% by weight, more preferably 0.01 to 1% by weight from the viewpoints of bringing about the high effects of preventing development of wrinkles and remedying the wrinkled skin, and of a feeling upon use and stability.

Of the skin activating ingredients as the component (B), examples of the singlet oxygen scavengers or antioxidants include carotenoides such as α-carotene, β-carotene, lycopene, cryptoxanthin, lutein, zeaxanthin, isozeaxanthin, rhodoxanthin, capsanthin and crocetin; 1,4-diazacyclooctane, 2,5-dimethylfuran, 2-methylfuran, 2,5-diphenylfuran, 1,3-diphenylisobenzofuran, α-tocopherol, β-tocopherol, γ-tocopherol, d-tocopherol, histidine, tryptophan, methionine and alanine or alkyl esters thereof; tannins such as dibutylhydroxytoluene, butylhydroxyanisole, ascorbic acid, tannic acid, epicatechin, epicarocatechin, epicatechin gallate and epicarocatechin gallate; and flavonoids such as rutin.

Of these, carotenes, tocopherols, ascorbic acid, tannic acid, epicatechin gallate and epicarocatechin gallate are preferred.

These singlet oxygen scavengers or antioxidants may be used either singly or in any combination thereof and are preferably incorporated in a proportion of 0.001 to 5% by weight based on the total weight of the composition. It is more preferable to incorporate them in a proportion of particularly 0.01 to 2% by weight, more preferably 0.01 to 1% by weight from the viewpoints of bringing about the high effects of preventing development of wrinkles and remedying the wrinkled skin, and of a feeling upon use and stability.

Of the skin activating ingredients as the component (B), examples of the water-soluble polymers include polysaccharides, acrylic polymers, etc. As the polysaccharides, acid polysaccharides are preferred, with modified hetero-polysaccharides described in, for example, Japanese Patent Application Laid-Open No. 10997/1989 being particularly preferred.

Examples of the acrylic polymers include Carbopol 941, 981, 940, 980, 1342 and 1382; Pemulane TR-1 and TR-2, and Sepigel 305.

Examples of other water-soluble polymers include guar gum, quince seed, carrageenan, locust bean gum, gum arabic, tragacanth gum, pectin, mannan, starch, sodium alginate, sodium hyaluronate, xanthan gum, pullulan, dextran, curdlan, collagen, keratin, casein, albumin, gelatin, chondroitin sulfate, chitin, cationic cellulose, hydroxyethyl cellulose, hydroxypropyl cellulose, hydroxypropylmethyl cellulose, hydroxyethyl cellulose, hydroxypropyltrimethylammonium chloride ether, carboxymethyl cellulose, dextran sulfate, carboxymethyl chitin, soluble starch, carboymethyl starch, propylene glycol alginate, polyvinyl alcohol, polyvinyl pyrrolidone, sodium polyacrylate and poly(vinyl methyl ether). Of these, xanthan gum, sodium hyaluronate and hydroxyethyl cellulose are particularly preferred.

These water-soluble polymers may be used either singly or in any combination thereof and are preferably incorporated in a proportion of 0.0001 to 30% by weight based on the total weight of the composition. It is more preferable to incorporate them in a proportion of particularly 0.001 to 20% by weight, more preferably 0.01 to 15% by weight, since a cosmetic composition which is excellent in the moisturizing effect, the effects of preventing and remedying skin roughness, and the effects of preventing and remedying spots and freckles, gives users a more pleasant feeling upon use, and has excellent stability can be provided.

Of the skin activating ingredients as the component (B), examples of the alcohols include higher alcohols. Of these, cetanol and stearyl alcohols are particularly preferred.

These higher alcohols may be used either singly or in any combination thereof and are preferably incorporated in a proportion of 0.01 to 20% by weight based on the total weight of the composition. It is more preferable to incorporate them in a proportion of particularly 0.05 to 10% by weight, more preferably 0.1 to 5% by weight, since a cosmetic composition which is enhanced in the moisturizing effect, the effects of preventing and remedying skin roughness, and the effects of preventing and remedying spots and freckles, gives users a more pleasant feeling upon use, and has excellent stability can be provided.

Of the skin activating ingredients as the component (B), examples of the water-soluble moisturizers include polyhydric alcohols, amino acids, sodium pyrrolidonecarboxylate, urea, lactic acid, hyaluronic acid and chemically modified collagen. Examples of the polyhydric alcohols include glycols such as ethylene glycol, 1,3-propanediol, polyethylene glycol, polypropylene glycol, dipropylene glycol, propylene glycol and butylene glycol; glycerol and polyglycerols such as diglycerol, triglycerol and tetraglycerol; and glucose, maltose, maltitol, sucrose, fructose, xylitol, sorbitol, maltotriose, threitol, erythritol, alcohols obtained by reduction of amylolytic sugar, sorbit and polyoxyalkylene alkylglucosides. Of these, glycols, glycerol and 1,3-propanediol are particularly preferred.

When one or more alcohols selected from among, in particular, polyethylene glycol, polypropylene glycol, dipropylene glycol, propylene glycol and butylene glycol of the above-mentioned glycols are incorporated, a cosmetic composition which is extremely high in moisturizing effect and can retain the effect longer can be provided.

These moisturizers may be used either singly or in any combination thereof and are preferably incorporated in a proportion of 0.001 to 90% by weight based on the total weight of the composition. It is more preferable to incorporate them in a proportion of particularly 0.01 to 50% by weight, more preferably 0.1 to 20% by weight, since a cosmetic composition which is enhanced in the moisturizing effect, the effects of preventing and remedying skin roughness, and the effects of preventing development of wrinkles and remedying the wrinkled skin, gives users a more pleasant feeling upon use, and has excellent stability can be provided.

The combined use of one or more of the above-described glycols with any other moisturizer having a solubility of at least 10% by weight, particularly at least 20% by weight in said glycols at 20° C. is preferred, since the resultant cosmetic composition can retained the moisturizing effect still longer.

Examples of the moisturizer having a solubility of at least 10% by weight in said glycols include natural moisturizing factors such as glycerol, sorbitol, maltitol, amino acids, sodium pyrrolidonecarboxylate, urea and lactic acid; and hyaluronic acid and chemically modified collagen. These moisturizers are preferably incorporated in a proportion of 0.1 to 25% by weight, particularly 1 to 20% by weight based on the total weight of the composition.

No particular limitation is imposed on the sterols of the skin activating ingredients as the component (B). However, preferable examples thereof include cholesterol, cholesteryl isostearate and cholesteryl alkenylsuccinates (Japanese Patent Application Laid-Open No. 294989/1993).

These sterols may be used either singly or in any combination thereof and are preferably incorporated in a proportion of 0.001 to 50% by weight based on the total weight of the composition. It is more preferable to incorporate them in a proportion of particularly 0.005 to 30% by weight, more preferably 0.01 to 20% by weight, since a cosmetic composition which is enhanced in the moisturizing effect, the effects of preventing and remedying skin roughness, and the effects of preventing development of wrinkles and remedying the wrinkled skin, gives users a more pleasant feeling upon use, and has excellent stability can be provided.

As the blood circulation-facilitating agents of the skin activating ingredients as the component (B), those commonly used in the classical cosmetic products, quasi-drugs, drugs and the like may be used as they are. In particular, examples of compounds used as such agents include esterified products, nicotinate and orotate of vitamin E, which are described as vasodilators in Japanese Patent Application Laid-Open No. 87506/1987; esterified products, acetate and succinate of vitamin E, which are described as periphery circulation-facilitating agents in Japanese Patent Application Laid-Open No. 195316/1987; and besides nicotinic acid amide, methyl nicotinate and the like.

As plant extracts having a blood circulation-facilitating effect, there may be used extracts which are clearly described as having a blood circulation-facilitating effect in "Fragrance Journal, Extra Edition Vol. 6 (1986)" and "Fragrance Journal, Extra Edition Vol. 1 (1979)", for example, plant extracts from arnica, Nippon hawthorn, quinine tree, scarlet sage, *Tilia europaea* L, *Panax ginseng* C. A. Meyer, juniper, rosemary, Saint-John's-wort, ginkgo, melissa, petty white-root, *marronnier*, Japanese green gentian, garlic, chamomile, cyme, Japanese mint, nettle, red pepper, ginger, hop, horse chestnut, lavender, carrot, brown mustard, cinnamon, pine, *Cnidii rhizoma*, elder, Japanese parsley, *Scopolia japonica* Maxlm, peony, myrica, *Houttuynia cordata*, candock, astringent persimmon, pot marigold, field poppy, gentian, grapes, *Glehnia littoralis*, bitter orange, citron, calamus, Watson pomelo, hamamelis, melilot, fennel, Japanese pepper tree, *Paeoniae radix*, eucalyptus, mugwort, *Isodon japonicus* Hara, rice, saphorae radix, ginger and clove.

These blood circulation-facilitating agents may be used either singly or in any combination thereof and are preferably incorporated in a proportion of generally 0.001 to 5% by weight in terms of active ingredients (dry solids in the case of plant extracts), based on the total weight of the composition. It is more preferable to incorporate them in a proportion of particularly 0.01 to 5% by weight, more preferably 0.05 to 3% by weight, since a cosmetic composition which is enhanced in the effects of preventing the firm and resilient skin from declining and remedying the declined skin, the effects of preventing a complexion from dulling and remedying a dull looking face, moisturizing effect, the effects of preventing and remedying skin roughness, the effects of preventing development of wrinkles and remedying the wrinkled skin, and the effects of preventing and remedying spots and freckles, gives users a more pleasant feeling upon use, and has far excellent stability can be provided.

As the sebum secretion inhibitors of the skin activating ingredients as the component (B), may be used, for example, anti-androgenic agents, crude drug extracts, astringents, hydroxy-fatty acids and the like, which are printed in "Fragrance Journal, No. 10 (1994)" and are in common use as sebum secretion inhibitors.

Specifically, examples of the anti-androgenic agents include oxendolone, 17-α-methyl-β-nortestosterone, chlormadinone acetate, cyproterone acetate, spironolactone, hydroxyflutamide, estradiol and ethinyl estradiol.

Examples of the crude drug extracts include extracts from leaves of walnut, pothos vine, sage, hop, rosemary, Saint-John's-wort, Japanese mint, chamomile, cashew, goldthread, Amur cork tree, OREI, *houttuyniae herba*, dried orange peel, carrot, *Paeoniae radix*, mat rush, propolis, *alismatis rhizoma*, tannin, hamamelis, peony and birch tar, and royal jelly and yeast extract.

Examples of the astringents include zinc sulfocarbolate, zinc oxide, aluminum hydroxychloride and (allantoinato) dihydroxyaluminum.

Examples of the hydroxy-fatty acids include 10-hydroxyundecanoic acid and 12-hydroxystearic acid.

Besides, vitamin $B_6$, 13-cis-retinoic acid, vitamin E, glycyrrhetinic acid, salicylic acid, nicotinic acid, calcium pantothenate, dicalcium azelate and the like may also be used as the sebum secretion inhibitors.

Of these, estradiol, zinc sulfocarbolate, zinc oxide, royal jelly, 10-hydroxyundecanoic acid and 12-hydroxy-stearic acid are particularly preferred.

When these sebum secretion inhibitors are incorporated, it is preferable to incorporate them in a proportion of particularly 0.01–10% by weight, more preferably 0.1–5% by weight (in terms of dry solids in the case of crude drug extracts) based on the total weight of the composition.

No particular limitation is imposed on the softening agents. However, examples thereof include α-hydroxy acids such as α-hydroxyisobutyric acid, α-hydroxyisocaproic acid, α-hydroxy-n-capronic acid, α-hydroxyisocaprylic acid, α-hydroxy-n-caprylic acid, α-hydroxy-n-capric acid, lactic acid, α-hydroxystearic acid, citric acid and glycolic acid; amines such as ε-aminocaproic acid, urea, 2-hydroxyguanidine and 2-(2-hydroxyethoxy)ethylguanidine; and beside peptides described in Japanese Patent Application Laid-Open Nos. 99315/1987 and 178207/1990, and trimethylglycine described in Japanese Patent Application Laid-Open No. 293625/1994.

These softening agents are preferably incorporated in a proportion of 0.05 to 10% by weight, particularly 0.2 to 5% by weight based on the total weight of the composition.

As the skin activating component of the component (B), the above-described various ingredients may be used either singly or in any combination thereof. The total amount thereof is preferably 5 to 60% by weight, particularly 10 to 40% by weight based on the total weight of the composition.

Into the cosmetics according to the present invention, various kinds of optional ingredients commonly used in the classical cosmetic products, quasi-drugs, drugs and the like may be suitably incorporated in addition to the above-described essential components, as needed, so far as no detrimental influence is thereby imposed on the effects of the present invention. Examples of such optional ingredients include purified water, ethanol, surfactants, oily ingredients, silicones, fluorine-containing oily substances, ultraviolet protecting agents, powder, oil gelling agents, film-forming agents, pH adjusters, inorganic salts, antiseptics, chelating agents, coloring matter and perfume bases.

The cosmetics according to the present invention can be prepared in accordance with a method known per se in the art. The cosmetics according to the present invention are not limited to general cosmetic skin-care compositions, and include quasi-drugs, external skin-care drugs and the like. The preparation forms thereof may also be optionally selected as necessary for the end application intended.

As the cosmetics according to the present invention, may be formulated cosmetic compositions of various forms including, for example, water/oil type emulsified cosmetics, oil/water type emulsified cosmetics, creams, cosmetic emulsions, toilet waters, oily cosmetics, packs, lip sticks, foundations, skin cleansers, hair tonics, hair dressing compositions, hair grooming compositions, hair growth stimulants, etc.

EXAMPLES

The present invention will hereinafter be described more specifically by the following Examples. However, the present invention is not limited to these Examples. Incidentally, all designations of "%" as will be used in the following examples mean % by weight unless expressly noted, and the incorporated amounts of plant extracts used in the examples were all expressed in terms of dry solids.

Example 1

Cosmetics of their corresponding formulations shown in Tables 1 to 6 were prepared in accordance with a method known per se in the art. The cosmetics thus obtained were used to evaluate them as to the moisturizing effect on the skin, the effects of preventing and remedying skin roughness, the effects of preventing the firm and resilient skin from declining and remedying the declined skin, the effects of preventing a complexion from dulling and remedying a dull looking face, the effects of preventing and remedying the conspicuousness of pores of the skin and pimples caused by excess sebum, microorganisms or keratonosis, the effects of preventing development of wrinkles and remedying the wrinkled skin, the effects of preventing and remedying spots and freckles, and a feeling upon use. The results are shown in Tables 1 to 6.

(Evaluation Method)

Moisturizing effect on the skin, the effects of preventing and remedying skin roughness, the effects of preventing the firm and resilient skin from declining and remedying the declined skin, the effects of preventing a complexion from dulling and remedying a dull looking face, the effects of preventing and remedying the conspicuousness of pores of the skin and pimples caused by excess sebum, microorganisms or keratonosis, the effects of preventing development of wrinkles and remedying the wrinkled skin, the effects of preventing and remedying spots and freckles, and a feeling upon use:

Twenty expert panelists were got to use each of the cosmetics, thereby organoleptically evaluating it in accordance with the following standard:

⊚: At least sixteen of 20 panelists judged to be good;
◯: Eleven to fifteen of 20 panelists judged to be good;
Δ: Six to ten of 20 panelists judged to be good;
X: At most five of 20 panelists judged to be good.

TABLE 1

| Component (%) | Invention product | | |
|---|---|---|---|
| | 1 | 2 | 3 |
| (1) Tris(butoxyethyl) phosphate | 10 | — | — |
| (2) Tris(butoxyethoxyethyl) phosphate | — | 10 | — |
| (3) Tris(butoxyethoxyethoxyethyl) phosphate | — | — | 10 |
| (4) Tris(ethoxyethoxyethyl) phosphate | — | — | — |
| (5) Tris(ethoxyethoxyethoxyethyl) phosphate | — | — | — |
| (6) Tris(methoxyethoxyethyl) phosphate | — | — | — |
| (7) Tris(methoxyethoxyethoxyethyl) phosphate | — | — | — |
| (8) Polyoxyethylene (60) hydrogenated castor oil | 2 | 2 | 2 |
| (9) Ceramide[1] | 3 | — | — |
| (10) Pseudoceramide[2] | — | 3 | — |
| (11) Pseudoceramide[3] | — | — | 3 |
| (12) Glycerol | 5 | — | 5 |
| (13) 1,3-Butylene glycol | — | 5 | — |
| (14) Arginine | 0.5 | 0.5 | 0.5 |
| (15) Hamamelis extract[4] | 1 | — | — |
| (16) Peony extract[5] | — | 1 | — |
| (17) *Thujopsis dolabrata* extract[6] | — | — | 1 |
| (18) Chamomile extract[7] | 0.5 | 0.5 | 0.5 |
| (19) Tea extract[8] | 0.5 | 0.5 | 0.5 |
| (20) Magnesium L-ascorbic acid phosphate | 2 | — | — |
| (21) Arbutin | — | 2 | — |
| (22) Kojic acid | — | — | 2 |
| (23) Stearyl glycyrrhetinate | 0.1 | 0.1 | 0.1 |
| (24) Cetanol | 0.3 | 0.3 | 0.3 |
| (25) Stearyl alcohol | 0.2 | 0.2 | 0.2 |
| (26) Acid hetero-polysaccharide[9] | 0.1 | 0.1 | 0.1 |
| (27) Acrylic polymer (Carbopol 981) | 0.3 | 0.3 | 0.3 |
| (28) Cholesterol | 1.0 | 1.0 | 1.0 |
| (29) dl-α-Tocopherol | 0.5 | 0.5 | 0.5 |
| (30) dl-α-Tocopherol nicotinate | 1 | — | — |
| (31) Nicotinic acid amide | — | 1 | — |
| (32) dl-α-Tocopherol acetate | — | — | 1 |
| (33) Maronnier extract[10] | — | — | — |
| (34) Rice germ oil | — | — | — |
| (35) Zinc sulfocarbolate | 1 | — | — |
| (36) Royal jelly | — | 1 | — |
| (37) 10-Hydroxyundecanoic acid | — | — | 1 |
| (38) Isopropylmethylphenol | — | — | — |
| (39) Salicylic acid | — | — | — |
| (40) Ethanol | 5.0 | 5.0 | 5.0 |
| (41) Perfume base | 0.1 | 0.1 | 0.1 |
| (42) Purified water | Bal. | Bal. | Bal. |
| Moisturizing effect | ⊚ | ⊚ | ⊚ |
| Effects of preventing and remedying skin roughness | ⊚ | ⊚ | ⊚ |
| Effects of preventing the firm and resilient skin from declining, remedying the declined skin, preventing a complexion from dulling and remedying a dull looking face | ⊚ | ⊚ | ⊚ |
| Effects of preventing and remedying the conspicuousness of pores of the skin and pimples | ⊚ | ⊚ | ⊚ |
| Effects of preventing development of wrinkles and remedying the wrinkled skin | ⊚ | ⊚ | ⊚ |
| Effects of preventing and remedying spots and freckles | ⊚ | ⊚ | ⊚ |
| Feeling upon use | ⊚ | ⊚ | ⊚ |

TABLE 2

| Component (%) | Invention product | | |
|---|---|---|---|
| | 4 | 5 | 6 |
| (1) Tris(butoxyethyl) phosphate | — | — | — |
| (2) Tris(butoxyethoxyethyl) phosphate | — | — | — |
| (3) Tris(butoxyethoxyethoxyethyl) phosphate | — | — | — |
| (4) Tris(ethoxyethoxyethyl) phosphate | 10 | — | — |
| (5) Tris(ethoxyethoxyethoxyethyl) phosphate | — | 10 | — |
| (6) Tris(methoxyethoxyethyl) phosphate | — | — | 10 |
| (7) Tris(methoxyethoxyethoxyethyl) phosphate | — | — | — |
| (8) Polyoxyethylene (60) hydrogenated castor oil | 2 | 2 | 2 |
| (9) Ceramide[1] | 3 | — | — |
| (10) Pseudoceramide[2] | — | 3 | — |
| (11) Pseudoceramide[3] | — | — | 3 |
| (12) Glycerol | — | 5 | — |
| (13) 1,3-Butylene glycol | 5 | — | 5 |
| (14) Arginine | 0.5 | 0.5 | 0.5 |
| (15) Hamamelis extract[4] | 1 | — | — |
| (16) Peony extract[5] | — | 1 | — |
| (17) *Thujopsis dolabrata* extract[6] | — | — | 1 |
| (18) Chamomile extract[7] | 0.5 | 0.5 | 0.5 |
| (19) Tea extract[8] | 0.5 | 0.5 | 0.5 |
| (20) Magnesium L-ascorbic acid phosphate | 2 | — | — |
| (21) Arbutin | — | 2 | — |
| (22) Kojic acid | — | — | 2 |
| (23) Stearyl glycyrrhetinate | 0.1 | 0.1 | 0.1 |
| (24) Cetanol | 0.3 | 0.3 | 0.3 |
| (25) Stearyl alcohol | 0.2 | 0.2 | 0.2 |
| (26) Acid hetero-polysaccharide[9] | 0.1 | 0.1 | 0.1 |
| (27) Acrylic polymer (Carbopol 981) | 0.3 | 0.3 | 0.3 |
| (28) Cholesterol | 1.0 | 1.0 | 1.0 |
| (29) dl-α-Tocopherol | 0.5 | 0.5 | 0.5 |
| (30) dl-α-Tocopherol nicotinate | — | — | 1 |
| (31) Nicotinic acid arriide | — | — | — |
| (32) dl-α-Tocopherol acetate | — | — | — |
| (33) Maronnier extract[10] | 1 | — | — |
| (34) Rice germ oil | — | 1 | — |
| (35) Zinc sulfocarbolate | — | — | — |
| (36) Royal jelly | — | — | — |
| (37) 10-Hydroxyundecanoic acid | — | — | 1 |
| (38) Isopropylmethylphenol | 0.1 | — | — |
| (39) Salicylic acid | — | 0.1 | — |
| (40) Ethanol | 5.0 | 5.0 | 5.0 |
| (41) Perfume base | 0.1 | 0.1 | 0.1 |
| (42) Purified water | Bal. | Bal. | Bal. |
| Moisturizing effect | ⊚ | ⊚ | ⊚ |
| Effects of preventing and remedying skin roughness | ⊚ | ⊚ | ⊚ |
| Effects of preventing the firm and resilient skin from declining, remedying the declined skin, preventing a complexion from dulling and remedying a dull looking face | ⊚ | ⊚ | ⊚ |

TABLE 2-continued

| Component (%) | Invention product | | |
|---|---|---|---|
| | 4 | 5 | 6 |
| Effects of preventing and remedying the conspicuousness of pores of the skin and pimples | ◎ | ◎ | ◎ |
| Effects of preventing development of wrinkles and remedying the wrinkled skin | ◎ | ◎ | ◎ |
| Effects of preventing and remedying spots and freckles | ◎ | ◎ | ◎ |
| Feeling upon use | ◎ | ◎ | ◎ |

TABLE 3

| Component (%) | Invention product 7 |
|---|---|
| (1) Tris(butoxyethyl) phosphate | — |
| (2) Tris(butoxyethoxyethyl) phosphate | — |
| (3) Tris(butoxyethoxyethoxyethyl) phosphate | — |
| (4) Tris(ethoxyethoxyethyl) phosphate | — |
| (5) Tris(ethoxyethoxyethoxyethyl) phosphate | — |
| (6) Tris(methoxyethoxyethyl) phosphate | — |
| (7) Tris(methoxyethoxyethoxyethyl) phosphate | 10 |
| (8) Polyoxyethylene (60) hydrogenated castor oil | 2 |
| (9) Ceramide[1] | 3 |
| (10) Pseudoceramide[2] | — |
| (11) Pseudoceramide[3] | — |
| (12) Glycerol | 5 |
| (13) 1,3-Butylene glycol | — |
| (14) Arginine | 0.5 |
| (15) Hamamelis extract[4] | 1 |
| (16) Peony extract[5] | — |
| (17) Thujopsis dolabrata extract[6] | — |
| (18) Chamomile extract[7] | 0.5 |
| (19) Tea extract[8] | 0.5 |
| (20) Magnesium L-ascorbic acid phosphate | 2 |
| (21) Arbutin | — |
| (22) Kojic acid | — |
| (23) Stearyl glycyrrhetinate | 0.1 |
| (24) Cetanol | 0.3 |
| (25) Stearyl alcohol | 0.2 |
| (26) Acid hetero-polysaccharide[9] | 0.1 |
| (27) Acrylic polymer (Carbopol 981) | 0.3 |
| (28) Cholesterol | 1.0 |
| (29) dl-α-Tocopherol | 0.5 |
| (30) dl-α-Tocopherol nicotinate | — |
| (31) Nicotinic acid amide | 1 |
| (32) dl-α-Tocopherol acetate | — |
| (33) Maronnier extract[10] | — |
| (34) Rice germ oil | — |
| (35) Zinc sulfocarbolate | 1 |
| (36) Royal jelly | — |
| (37) 10-Hydroxyundecanoic acid | — |
| (38) Isopropylmethylphenol | — |
| (39) Salicylic acid | — |
| (40) Ethanol | 5.0 |
| (41) Perfume base | 0.1 |
| (42) Purified water | Balance |
| Moisturizing effect | ◎ |
| Effects of preventing and remedying skin roughness | ◎ |
| Effects of preventing the firm and resilient skin from declining, remedying the declined skin, preventing a complexion from dulling and remedying a dull looking face | ◎ |
| Effects of preventing and remedying the conspicuousness of pores of the skin and pimples | ◎ |
| Effects of preventing development of wrinkles and remedying the wrinkled skin | ◎ |
| Effects of preventing and remedying spots and freckles | ◎ |
| Feeling upon use | ◎ |

TABLE 4

| Component (%) | Comparative product | | |
|---|---|---|---|
| | 1 | 2 | 3 |
| (1) Tris(butoxyethyl) phosphate | — | — | — |
| (2) Tris(butoxyethoxyethyl) phosphate | — | — | — |
| (3) Tris(butoxyethoxyethoxyethyl) phosphate | — | — | — |
| (4) Tris(ethoxyethoxyethyl) phosphate | — | — | — |
| (5) Tris(ethoxyethoxyethoxyethyl) phosphate | — | — | — |
| (6) Tris(methoxyethoxyethyl) phosphate | — | — | — |
| (7) Tris(methoxyethoxyethoxyethyl) phosphate | — | — | — |
| (8) Polyoxyethylene (60) hydrogenated castor oil | 2 | 2 | 2 |
| (9) Ceramide[1] | 3 | — | 3 |
| (10) Pseudoceramide[2] | — | — | — |
| (11) Pseudoceramide[3] | — | — | — |
| (12) Glycerol | — | — | 5 |
| (13) 1,3-Butylene glycol | 5 | — | — |
| (14) Arginine | 0.5 | 0.5 | 0.5 |
| (15) Hamamelis extract[4] | 1 | 1 | — |
| (16) Peony extract[5] | — | — | 1 |
| (17) Thujopsis dolabrata extract[6] | — | — | — |
| (18) Chamomile extract[7] | 0.5 | 0.5 | 0.5 |
| (19) Tea extract[8] | 0.5 | 0.5 | 0.5 |
| (20) Magnesium L-ascorbic acid phosphate | 2 | — | — |
| (21) Arbutin | — | 2 | — |
| (22) Kojic acid | — | — | 2 |
| (23) Stearyl glycyrrhetinate | 0.1 | 0.1 | 0.1 |
| (24) Cetanol | 0.3 | 0.3 | 0.3 |
| (25) Stearyl alcohol | 0.2 | 0.2 | 0.2 |
| (26) Acid hetero-polysaccharide[9] | 0.1 | 0.1 | 0.1 |
| (27) Acrylic polymer (Carbopol 981) | 0.3 | 0.3 | 0.3 |
| (28) Cholesterol | 1.0 | 1.0 | 1.0 |
| (29) dl-α-Tocopherol | 0.5 | 0.5 | 0.5 |
| (30) dl-α-Tocopherol nicotinate | 1 | — | — |
| (31) Nicotinic acid amide | — | 1 | — |
| (32) dl-α-Tocopherol acetate | — | — | 1 |
| (33) Maronnier extract[10] | — | — | — |
| (34) Rice germ oil | — | — | — |
| (35) Zinc sulfocarbolate | 1 | — | — |
| (36) Royal jelly | — | 1 | — |
| (37) 10-Hydroxyundecanoic acid | — | — | 1 |
| (38) Isopropylmethylphenol | — | — | — |
| (39) Salicylic acid | — | — | — |
| (40) Ethanol | 5.0 | 5.0 | 5.0 |
| (41) Perfume base | 0.1 | 0.1 | 0.1 |
| (42) Purified water | Bal. | Bal. | Bal. |
| Moisturizing effect | ○ | Δ | ○ |
| Effects of preventing and remedying skin roughness | ○ | ○ | Δ |
| Effects of preventing the firm and resilient skin from declining, remedying the declined skin, preventing a complexion from dulling and remedying a dull looking face | ○ | ○ | ○ |
| Effects of preventing and remedying the conspicuousness of pores of the skin and pimples | ○ | ○ | ○ |
| Effects of preventing development of wrinkles and remedying the wrinkled skin | ○ | ○ | ○ |
| Effects of preventing and remedying spots and freckles | ○ | ○ | ○ |
| Feeling upon use | Δ | ○ | Δ |

TABLE 5

| Component (%) | Comparative product | | |
|---|---|---|---|
| | 4 | 5 | 6 |
| (1) Tris(butoxyethyl) phosphate | — | — | — |
| (2) Tris(butoxyethoxyethyl) phosphate | — | — | — |
| (3) Tris(butoxyethoxyethoxyethyl) phosphate | — | — | — |
| (4) Tris(ethoxyethoxyethyl) phosphate | — | — | — |
| (5) Tris(ethoxyethoxyethoxyethyl) phosphate | — | — | — |
| (6) This(methoxyethoxyethyl) phosphate | — | — | — |
| (7) This(methoxyethoxyethoxyethyl) phosphate | — | — | — |

TABLE 5-continued

| Component (%) | Comparative product 4 | Comparative product 5 | Comparative product 6 |
|---|---|---|---|
| (8) Polyoxyethylene (60) hydrogenated castor oil | 2 | 2 | 2 |
| (9) Ceramide[1] | — | — | 3 |
| (10) Pseudoceramide[2] | 3 | — | — |
| (11) Pseudoceramide[3] | — | 3 | — |
| (12) Glycerol | — | 5 | — |
| (13) 1,3-Butylene glycol | 5 | — | 5 |
| (14) Arginine | 0.5 | 0.5 | 0.5 |
| (15) Hamamelis extract[4] | — | — | 1 |
| (16) Peony extract[5] | — | — | — |
| (17) *Thujopsis dolabrata* extract[6] | — | 1 | — |
| (18) Chamomile extract[7] | 0.5 | 0.5 | 0.5 |
| (19) Tea extract[8] | 0.5 | 0.5 | 0.5 |
| (20) Magnesium L-ascorbic acid phosphate | 2 | — | — |
| (21) Arbutin | — | — | — |
| (22) Kojic acid | — | — | 2 |
| (23) Stearyl glycyrrhetinate | 0.1 | 0.1 | 0.1 |
| (24) Cetanol | 0.3 | 0.3 | 0.3 |
| (25) Stearyl alcohol | 0.2 | 0.2 | 0.2 |
| (26) Acid hetero-polysaccharide[9] | 0.1 | 0.1 | 0.1 |
| (27) Acrylic polymer (Carbopol 981) | 0.3 | 0.3 | 0.3 |
| (28) Cholesterol | 1.0 | 1.0 | 1.0 |
| (29) dl-α-Tocopherol | 0.5 | 0.5 | 0.5 |
| (30) dl-α-Tocopherol nicotinate | — | — | — |
| (31) Nicotinic acid amide | — | — | — |
| (32) dl-α-Tocopherol acetate | — | — | — |
| (33) Maronnier extract[10] | 1 | — | — |
| (34) Rice germ oil | — | 1 | — |
| (35) Zinc sulfocarbolate | — | — | — |
| (36) Royal jelly | — | — | — |
| (37) 10-Hydroxyundecanoic acid | — | — | 1 |
| (38) Isopropylmethylphenol | 0.1 | — | — |
| (39) Salicylic acid | — | 0.1 | — |
| (40) Ethanol | 5.0 | 5.0 | 5.0 |
| (41) Perfume base | 0.1 | 0.1 | 0.1 |
| (42) Purified water | Bal. | Bal. | Bal. |
| Moisturizing effect | ◯ | ◯ | ◯ |
| Effects of preventing and remedying skin roughness | ◯ | ◯ | ◯ |
| Effects of preventing the firm and resilient skin from declining, remedying the declined skin, preventing a complexion fran dulling and remedying a dull looking face | ◯ | ◯ | Δ |
| Effects of preventing and remedying the conspicuousness of pores of the skin and pimples | ◯ | ◯ | ◯ |
| Effects of preventing development of wrinkles and remedying the wrinkled skin | Δ | ◯ | ◯ |
| Effects of preventing and remedying spots and freckles | ◯ | Δ | ◯ |
| Feeling upon use | Δ | Δ | Δ |

TABLE 6

| Component (%) | Comparative product 7 |
|---|---|
| (1) Tris(butoxyethyl) phosphate | — |
| (2) Tris(butoxyethoxyethyl) phosphate | — |
| (3) Tris(butoxyethoxyethoxyethyl) phosphate | — |
| (4) Tris(ethoxyethoxyethyl) phosphate | — |
| (5) Tris(ethoxyethoxyethoxyethyl) phosphate | — |
| (6) Tris(methoxyethyl) phosphate | — |
| (7) Tris(methoxyethoxyethyl) phosphate | — |
| (8) Polyoxyethylene (60) hydrogenated castor oil | 2 |
| (9) Ceramide[1] | — |
| (10) Pseudoceramide[2] | 3 |
| (11) Pseudoceramide[3] | — |
| (12) Glycerol | 5 |
| (13) 1,3-Butylene glycol | — |
| (14) Arginine | 0.5 |
| (15) Hamamelis extract[4] | — |
| (16) Peony extract[5] | 1 |
| (17) *Thujopsis dolabrata* extract[6] | — |
| (18) Chamomile extract[7] | 0.5 |
| (19) Tea extract[8] | 0.5 |
| (20) Magnesium L-ascorbic acid phosphate | — |
| (21) Arbutin | — |
| (22) Kojic acid | 2 |
| (23) Stearyl glycyrrhetinate | 0.1 |
| (24) Cetanol | 0.3 |
| (25) Stearyl alcohol | 0.2 |
| (26) Acid hetero-polysaccharide[9] | 0.1 |
| (27) Acrylic polymer (Carbopol 981) | 0.3 |
| (28) Cholesterol | 1.0 |
| (29) dl-α-Tocopherol | 0.5 |
| (30) dl-α-Tocopherol nicotinate | 1 |
| (31) Nicotinic acid amide | — |
| (32) dl-α-Tocopherol acetate | — |
| (33) Maronnier extract[10] | — |
| (34) Rice germ oil | — |
| (35) Zinc sulfocarbolate | — |
| (36) Royal jelly | — |
| (37) 10-Hydroxyundecanoic acid | — |
| (38) Isopropylmethylphenol | — |
| (39) Salicylic acid | — |
| (40) Ethanol | 5.0 |
| (41) Perfume base | 0.1 |
| (42) Purified water | Balance |
| Moisturizing effect | ◯ |
| Effects of preventing and remedying skin roughness | ◯ |
| Effects of preventing the firm and resilient skin from declining, remedying the declined skin, preventing a complexion from dulling and remedying a dull looking face | ◯ |
| Effects of preventing and remedying the conspicuousness of pores of the skin and pimples | Δ |
| Effects of preventing development of wrinkles and remedying the wrinkled skin | ◯ |
| Effects of preventing and remedying spots and freckles | ◯ |
| Feeling upon use | Δ |

[1]In the general formula (2), a compound of $R^4 = C_{15}H_{31}$, and $R^5 = CH_3(CH_2)_{16}\!=\!CH$.
[2]In the general formula (3), a compound of $R^6 = C_{16}H_{33}$, $R^7 = C_{15}H_{31}$, a = b = d = 0, and c = 1.
[3]In the general formula (4), a compound of $R^8 = C_{16}H_{33}$, $R^9 = C_{13}H_{27}$, $R^{10} = C_3H_6$, and $R^{11} = OCH_3$.
[4]Hamamelis Liquid (product of Ichimaru Pharcos Co., Ltd.).
[5]Pharcolex Botanpi E (product of Ichimaru Pharcos Co., Ltd.).
[6]*Thujopsis dolabrata* extract (product of Ichimaru Pharcos Co., Ltd.).
[7]Chamomile extract (product of Maruzen Seiyaku K.K.).
[8]Green Tea Liquid (product of Ichimaru Pharcos Co., Ltd.).
[9]An acid hetero-polysaccharide derived from the callus of tuberose prepared in accordance with Example 1 of Japanese Patent Application Laid-Open No. 10997/1989.
[10]Maronnier Extract BG (product of Maruzen Seiyaku K.K.).

Apparent from the results shown in Tables 1 to 6, all the cosmetics according to the present invention were synergistically enhanced in the moisturizing effect, the effects of preventing and remedying skin roughness, the effects of preventing the firm and resilient skin from declining and remedying the declined skin, the effects of preventing a complexion from dulling and remedying a dull looking face, the effects of preventing and remedying the conspicuousness of pores of the skin and pimples caused by excess sebum, microorganisms or keratonosis, the effects of preventing development of wrinkles and remedying the wrinkled skin, and the effects of preventing and remedying spots and freckles compared with the conventional cosmetics, and showed good results even in a feeling upon use.

Example 2

Cosmetics of their corresponding formulations shown in Table 7 were prepared to determine the retention of their moisturizing effects.

TABLE 7

| Component (wt. %) | Invention product | | | | Comparative product | | | | |
|---|---|---|---|---|---|---|---|---|---|
| | 8 | 9 | 10 | 11 | 8 | 9 | 10 | 11 | 12 |
| (1) Bis(butoxy-ethoxyethyl)-ethyl phosphate | 50 | 25 | — | — | 100 | — | — | — | — |
| (2) Tris(butoxy-ethyl) phosphate | — | — | 50 | 25 | — | 100 | — | — | — |
| (3) Dipropylene glycol | 50 | 50 | 50 | 50 | — | — | 100 | — | — |
| (4) Glycerol | — | 25 | — | 25 | — | — | — | 100 | — |
| (5) Purified water | — | — | — | — | — | — | — | — | 100 |

<Testing Method>

A fixed amount of each of the above samples was applied to the lower inner arm of a volunteer and washed off with hot water after left at rest for 1 hour. The volunteer was got to enter an air-conditioned room kept at a temperature of 20° C. and a humidity of 30%. Fifteen minutes after that, the water content in the horny layer of the volunteer was measured by an impedance meter (manufactured by IBS Company). After additional 3 hours, the treated arm was washed with hot water again. Fifty minutes after that, the water content was measured in the same manner as described above. The results are shown in Table 8. The values shown in the table were average values (N=10).

TABLE 8

| Retention of* moisturizing effect | Invention product | | | | Comparative product | | | | |
|---|---|---|---|---|---|---|---|---|---|
| | 8 | 9 | 10 | 11 | 8 | 9 | 10 | 11 | 12 |
| After 15 min. | 105 | 110 | 105 | 110 | 70 | 70 | 65 | 75 | 60 |
| After 3 hr. | 65 | 75 | 65 | 80 | 40 | 40 | 35 | 45 | 40 |

*The unit is $\mu\Omega^{-1}$.

As apparent from Table 8, the mixed systems of phosphoric triester/dipropylene glycol in the invention products 8 and 10 were excellent in the moisturizing effect and the retention thereof compared with the cosmetics in which the phosphoric triester and dipropylene glycol were separately incorporated, and so it was proved that both components synergistically act. It was confirmed from the invention products 9 and 11 that the addition of glycerol is also effective.

Example 3

Creams of their corresponding formulations shown in Table 9 were prepared to determine the retention of their moisturizing effects.

TABLE 9

| Component (wt. %) | Invention product | | Comp. product |
|---|---|---|---|
| | 12 | 13 | 13 |
| (1) Vaseline | 6.0 | 6.0 | 6.0 |
| (2) Cetanol | 3.0 | 3.0 | 3.0 |
| (3) Lipophilic glycerol monostearate | 2.0 | 2.0 | 2.0 |
| (4) Polyoxyethylene sorbitan monoglycerate (20 E.O.) | 2.0 | 2.0 | 2.0 |
| (5) Bis(butoxyethoxyethyl)-ethyl phosphate | 20.0 | — | — |
| (6) Tris(butoxyethyl) phosphate | — | 20.0 | — |
| (7) Olive oil | — | — | 20.0 |
| (8) Butylparaben | 0.1 | 0.1 | 0.1 |
| (9) Methylparaben | 0.1 | 0.1 | 0.1 |
| (10) Dipropylene glycol | 10.0 | 10.0 | 10.0 |
| (11) Perfume base | 0.1 | 0.1 | 0.1 |
| (12) Purified water | Balance | Balance | Balance |

<Preparation Process>

The oil-phase components (1) to (8) were mixed and heated to melt them. The melt was kept at 70° C., while the water-phase components (9) to (12) were gradually added to the melt. The resultant mixture was emulsified by an emulsifier. The emulsion was cooled down to a final temperature of 25° C., thereby preparing a cream.

<Testing Method>

A fixed amount of each of the above samples was applied to the lower inner arm of a volunteer and washed off with hot water after left at rest for 2 hours. The volunteer was got to enter an air-conditioned room kept at a temperature of 20° C. and a humidity of 40%. Fifteen minutes after that, the water content in the horny layer of the volunteer was measured by an impedance meter (manufactured by IBS Company). One hour, 2 hours and 5 hours after the first washing with hot water, the treated arm was washed with hot water likewise to measure the water content in the horny layer after each washing. The results are shown in Table 10. The values shown in the table were average values (N=5).

TABLE 10

| Retention of* moisturizing effect | Invention product | | | Comp. product |
|---|---|---|---|---|
| | 12 | 13 | Blank | 13 |
| Right after first washing | 91 | 90 | 33 | 60 |
| After 1 hour | 80 | 78 | 33 | 55 |
| After 2 hours | 65 | 64 | 34 | 49 |
| After 5 hours | 55 | 55 | 31 | 38 |

*The unit is $\mu\Omega^{-1}$.

As apparent from Table 10, it was proved that the creams of the invention products 12 and 13 have a high moisturizing effect and are excellent in the retention thereof.

Industrial Applicability

The cosmetics according to the present invention are synergistically enhanced in moisturizing effect, the effects of preventing and remedying skin roughness, the effects of preventing the firm and resilient skin from declining and remedying the declined skin, the effects of preventing a complexion from dulling and remedying a dull looking face, the effects of preventing and remedying the conspicuousness of pores of the skin and pimples caused by excess sebum, microorganisms or keratonosis, the effects of preventing development of wrinkles and remedying the wrinkled skin, and the effects of preventing and remedying spots and freckles by using the phosphoric triester of the component (A) and the skin activating component of the component (B) in combination, and moreover give users a pleasant feeling upon use and have excellent stability.

What is claimed is:

1. A cosmetic composition comprising the following components (A) and (B):

(A) at least one phosphoric triester represented by the general formula (1):

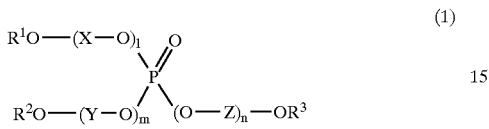

wherein $R^1$ and $R^2$ are the same or different from each other and independently a linear or branched alkyl group having 2 to 6 carbon atoms; $R^3$ is a linear or branched alkyl group having 2 to 4 carbon atoms; X and Y are both ethylene groups; is a linear or branched alkylene group having 2 or 3 carbon atoms; l and m are the same or different from each other and independently a number of 1 to 5, and n is a number of 0; and (B) a skin activating component, wherein the component (B) is at least one selected from the group consisting of ceramides, pseudoceramides, hydrophilic moisturizers exclusive of glycols and glycerol, amino acids, plant extracts, whitening agents, anti-inflammatory agents, singlet oxygen scavengers, antioxidants, water-soluble polysaccharides, water-soluble acrylic polymers, xanthan gum, sodium hyaluronate, hydroxyethylcellulose, higher alcohols, sterols, blood circulation-facilitating agents, sebum secretion inhibitors, softening agents, anti-microbial agents and keratolytic agents, wherein the anti-microbial agents are selected from the group consisting of sulfur, triclosan, trichlorocarbanilide, chlorhexidine hydrochloride, benzalkonium chloride, benzethonium chloride, cetylpyridinium chloride, benzalkonium alkyiphosphates, isopropylmethylphenol, benzoic acid, photosensitive element No. 201 and resorcin, and wherein the phosphoric triester is present in an amount that enhances the effect of the skin activating component when applied to the skin.

2. The cosmetic composition according to claim 1, wherein the effect is selected from the group consisting of a moisturizing effect, effects of treating skin roughness, effects of treating a dull looking face, effects of treating the conspicuousness of pores of the skin and pimples caused by excess sebum, microorganisms or keratonosis, effects of treating wrinkled skin, and effects of treating spots and freckles.

3. The cosmetic composition according to claim 1, wherein the phosphoric triester is present in an amount of 1 to 50% by weight of the composition.

4. The cosmetic composition according to claim 3, wherein the phosphoric triester is present in an amount of 2 to 25% by weight of the composition.

* * * * *

UNITED STATES PATENT AND TRADEMARK OFFICE
CERTIFICATE OF CORRECTION

PATENT NO. : 6,932,975 B2
DATED : August 23, 2005
INVENTOR(S) : Shinji Ishikawa et al.

It is certified that error appears in the above-identified patent and that said Letters Patent is hereby corrected as shown below:

Column 21,
Line 23, "groups; is" should read -- groups; Z is --.

Signed and Sealed this

Fifteenth Day of November, 2005

JON W. DUDAS
*Director of the United States Patent and Trademark Office*